US00PP28179P3

(12) United States Plant Patent
Stemkens

(10) Patent No.: US PP28,179 P3
(45) Date of Patent: Jul. 11, 2017

(54) ***ACHILLEA* PLANT NAMED 'ACBZ0002'**

(50) Latin Name: *Achillea millefolium*
Varietal Denomination: ACBZ0002

(71) Applicant: Henricus Godefridus Wilhelmus Stemkens, Enkhuizen (NL)

(72) Inventor: Henricus Godefridus Wilhelmus Stemkens, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 4 days.

(21) Appl. No.: 14/545,696

(22) Filed: Jun. 6, 2015

(65) Prior Publication Data

US 2016/0360668 P1 Dec. 8, 2016

(51) Int. Cl.
*A01H 5/02* (2006.01)

(52) U.S. Cl.
USPC ..... Plt./263.1

(58) Field of Classification Search
USPC ..... Plt./263.1
CPC ..... A01H 5/02
See application file for complete search history.

(56) References Cited

PUBLICATIONS

GTITM UPOVROM Plant Variety Database Citation for 'ACBZ0002' as per QZ PBR 20122014; Sep. 24, 2012.*

* cited by examiner

*Primary Examiner* — Kent L Bell
(74) *Attorney, Agent, or Firm* — C. A. Whealy

(57) ABSTRACT

A new and distinct cultivar of *Achillea* plant named 'ACBZ0002', characterized by its upright and uniform plant habit; moderately vigorous growth habit; freely branching habit; freely flowering habit with plants remaining in flower for a long period time; inflorescences with bright yellow-colored ray florets; and good garden performance.

2 Drawing Sheets

Botanical designation: *Achillea millefolium.*
Cultivar denomination: 'ACBZ0002'.

BACKGROUND OF THE INVENTION

The present invention relates to a new and distinct cultivar of *Achillea* plant, botanically known as *Achillea millefolium*, and hereinafter referred to by the name 'ACBZ0002'.

The new *Achillea* plant is a product of a planned breeding program conducted by the Inventor in Enkhuizen, The Netherlands. The objective of the breeding program is to create new early-flowering *Achillea* plants with uniform plant habit and large inflorescences with bright yellow-colored ray florets.

The new *Achillea* plant originated from a cross-pollination made by the Inventor in Enkhuizen, The Netherlands in July, 2007 of a proprietary selection of *Achillea millefolium* identified as code number H4981-13, not patented, as the female, or seed, parent with *Achillea millefolium* 'Moonshine', not patented, as the male, or pollen, parent. The new *Achillea* plant was discovered and selected by the Inventor as a single flowering plant from within the progeny of the stated cross-pollination in a controlled greenhouse environment in Enkhuizen, The Netherlands in July, 2008.

Asexual reproduction of the new *Achillea* plant by vegetative tip cuttings in a controlled environment in Enkhuizen, The Netherlands since August, 2008, has shown that the unique features of this new *Achillea* plant are stable and reproduced true to type in successive generations.

SUMMARY OF THE INVENTION

Plants of the new *Achillea* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'ACBZ0002'. These characteristics in combination distinguish 'ACBZ0002' as a new and distinct *Achillea* plant:

1. Upright and uniform plant habit.
2. Moderately vigorous growth habit.
3. Freely branching habit.
4. Freely flowering habit with plants remaining in flower for a long period time.
5. Inflorescences with bright yellow-colored ray florets.
6. Good garden performance.

Plants of the new *Achillea* differ from plants of the female parent selection in the following characteristics:

1. Plants of the new *Achillea* are taller than plants of the female parent selection.
2. Plants of the new *Achillea* are not as freely branching as plants of the female parent selection.
3. Inflorescences of plants of the new *Achillea* are longer lasting than inflorescences of plants of the female parent selection.

Plants of the new *Achillea* differ from plants of the male parent, 'Moonshine', in the following characteristics:

1. Plants of the new *Achillea* are more compact than and not as vigorous as plants of 'Moonshine'.
2. Plants of the new *Achillea* are more freely branching than plants of 'Moonshine'.
3. Plants of the new *Achillea* flower earlier than plants of 'Moonshine'.

4. Plants of the new *Achillea* have larger inflorescences than plants of 'Moonshine'.

Plants of the new *Achillea* can be compared to plants of *Achillea tomentosa*×*Achillea millefolium* 'Desyel', disclosed in U.S. Plant Pat. No. 22,369. In side-by-side comparisons conducted in Enkhuizen, The Netherlands, plants of the new *Achillea* differed from plants of 'Desyel' in the following characteristics:

1. Plants of the new *Achillea* were taller than plants of 'Desyel'.
2. Plants of the new *Achillea* were not as freely branching as plants of 'Desyel'.
3. Inflorescences of plants of the new *Achillea* were longer lasting than inflorescences of plants of 'Desyel'.

BRIEF DESCRIPTION OF THE PHOTOGRAPHS

The accompanying photographs illustrate the overall appearance of the new *Achillea* plant showing the colors as true as it is reasonably possible to obtain in colored reproductions of this type. Colors in the photographs may differ slightly from the color values cited in the detailed botanical description which accurately describe the colors of the new *Achillea* plant.

The photograph on the first sheet is a side perspective view of a typical flowering plant of 'ACBZ0002' grown in a container.

The photograph on the second sheet is a close-up view of a typical flowering plant of 'ACBZ0002'.

DETAILED BOTANICAL DESCRIPTION

Plants used for the aforementioned photographs and following observations and measurements describe plants grown during the late spring and summer in 13-cm containers in an outdoor nursery in Enkhuizen, The Netherlands and under cultural practices typical of commercial *Achillea* production. During the production of the plants, day temperatures ranged from 15° C. to 25° C. and night temperatures ranged from 5° C. to 15° C. Plants were 14 weeks old when the photographs and description were taken. In the following description, color references are made to The Royal Horticultural Society Colour Chart, 2007 Edition, except where general terms of ordinary dictionary significance are used.

Botanical classification: *Achillea millefolium* 'ACBZ0002'.

Parentage:

*Female, or seed, parent*.—Proprietary selection of *Achillea millefolium* identified as code number H4981-13, not patented.

*Male, or pollen, parent*.—Proprietary selection of *Achillea millefolium* 'Moonshine', not patented.

Propagation:

*Type*.—Terminal vegetative cuttings.

*Time to initiate roots, summer*.—About seven days at temperatures about 24° C.

*Time to initiate roots, winter*.—About nine days at temperatures about 20° C.

*Time to produce a rooted cutting, summer*.—About 18 days at temperatures about 24° C.

*Time to produce a rooted cutting, winter*.—About 21 days at temperatures about 20° C.

*Root description*.—Medium in thickness, fibrous; white in color.

*Rooting habit*.—Freely branching habit; medium density.

Plant description:

*Plant form/growth habit*.—Upright and uniform plant habit; strong and sturdy plants; moderately vigorous growth habit.

*Plant height*.—About 33 cm.

*Plant diameter or spread*.—About 30 cm to 33 cm.

*Lateral branches*.—Length: About 30 cm to 33 cm. Diameter: About 4 mm. Internode length: About 2 cm to 3 cm. Aspect: Mostly upright to slightly slanting outwardly. Strength: Strong, sturdy. Texture: Tomentose. Color: Close to 147C.

Leaf description:

*Arrangement*.—Alternate, simple; sessile.

*Leaf length*.—About 3.5 cm to 11 cm.

*Leaf width*.—About 1.5 cm.

*Leaflet length*.—About 4 mm to 10 mm.

*Leaflet width*.—About 2 mm to 6 mm.

*Leaf shape*.—Pinnate; feather-like lanceolate.

*Leaflet shape*.—Lanceolate; divergently lobed to divided.

*Leaf apex*.—Acute.

*Leaflet apex*.—Acute.

*Leaf base*.—Hastate.

*Leaflet base*.—Truncate.

*Leaflet margin*.—Dentate to laciniate.

*Texture, upper and lower surfaces*.—Sericeous.

*Venation pattern*.—Pinnate.

*Color*.—Developing leaves, upper surface: Close to 137B. Developing leaves, lower surface: Close to N138A. Fully expanded leaves, upper surface: Close to 137A; venation, close to 142B. Fully expanded leaves, lower surface: Close to 137C; venation, close to 142C.

Inflorescence description:

*Flowering arrangement and habit*.—Rotate composite inflorescence form; inflorescences arranged in terminal or axillary compound corymbs; corymbs are somewhat flat-topped; freely flowering habit with about 13 to 16 corymbs per plant; corymbs positioned above the foliar plane and face mostly upright.

*Fragrance*.—Rather unpleasant.

*Time to flower*.—Plants begin flowering during the late spring and early summer in The Netherlands and continue to flower throughout the summer; inflorescences not persistent; inflorescences maintain color and are long-lasting.

*Inflorescence buds*.—Height: About 7 mm. Diameter: About 4 mm. Shape: Ovate. Color: Close to 139C to 139D.

*Compound corymb diameter*.—About 13 cm.

*Compound corymb height*.—About 2 cm to 3 cm.

*Inflorescence diameter*.—About 9 mm.

*Disc diameter*.—About 2 mm.

*Receptacle diameter*.—About 4 mm.

*Receptacle height*.—About 5 mm.

*Receptacle shape*.—Rounded conical.

*Receptacle color*.—Close to 147D.

*Ray florets*.—Length: About 4 mm. Width: About 5 mm. Shape: Roughly orbicular. Apex: Truncate; repand. Base: Fused into a short tube. Margin: Entire. Texture, upper and lower surfaces: Smooth, glabrous. Number of ray florets per inflorescence: Five in a single whorl. Aspect: Mostly horizontal; flat to convex. Color: When opening, upper surface:

Close to 6A. When opening, lower surface: Close to 6C. Fully opened, upper surface: Close to 6A. Fully opened, lower surface: Close to 7D.

*Disc florets*.—Arrangement: Massed in the center of the receptacle. Length: About 6 mm. Diameter: About 1 mm. Shape: Tubular; apex, five-pointed. Number of disc florets per inflorescence: About 12 to 16. Texture: Smooth, glabrous. Color, immature: Apex: Close to 7A. Mid-section and base: Close to 157B. Color, mature: Apex: Close to 7A. Mid-section: Close to 157B. Base: Close to 155C.

*Phyllaries*.—Quantity per inflorescence: About 10 to 15 in about four whorls; imbricate. Length: About 3.5 mm. Width: About 1.5 mm to 2 mm. Shape: Ovate. Apex: Acute. Base: Fused. Margin: Entire. Texture, upper surface: Velutinous. Texture, lower surface: Smooth; glabrous. Color, upper surface: Close to 143B; margins, close to 200A. Color, lower surface: Close to 143B.

*Peduncles*.—Length: About 3 cm to 4 cm. Diameter: About 3 mm. Strength: Strong. Aspect: Mostly upright to slightly slanting. Texture: Sericeous. Color: Close to 147C.

*Reproductive organs* (*present on disc florets only*).—Androecium: Quantity of stamens per disc floret: About five. Filament length: About 4 mm. Filament color: Close to 157B. Anther shape: Ligulate. Anther length: About 2 mm. Anther color: Close to 7A. Pollen amount: Moderate. Pollen color: Close to 7A. Gynoecium: Quantity of pistils per disc floret: One. Pistil length: About 5 mm. Stigma shape: Bi-parted. Stigma color: Close to 7C. Style length: About 4 mm. Style color: Close to 157B. Ovary color: Close to N144C.

*Seeds and fruits*.—Seed and fruit production has not been observed on plants of the new *Achillea*.

Disease & pest resistance: Plants of the new *Achillea* have not been shown to be resistant to pathogens and pests common to *Achillea* plants.

Garden performance: Plants of the new *Achillea* have been observed to have good garden performance and tolerate wind, rain and to tolerate high temperatures about 35° C. and to be hardy to USDA Hardiness Zone 6.

It is claimed:

1. A new and distinct *Achillea* plant named 'ACBZ0002' as illustrated and described.

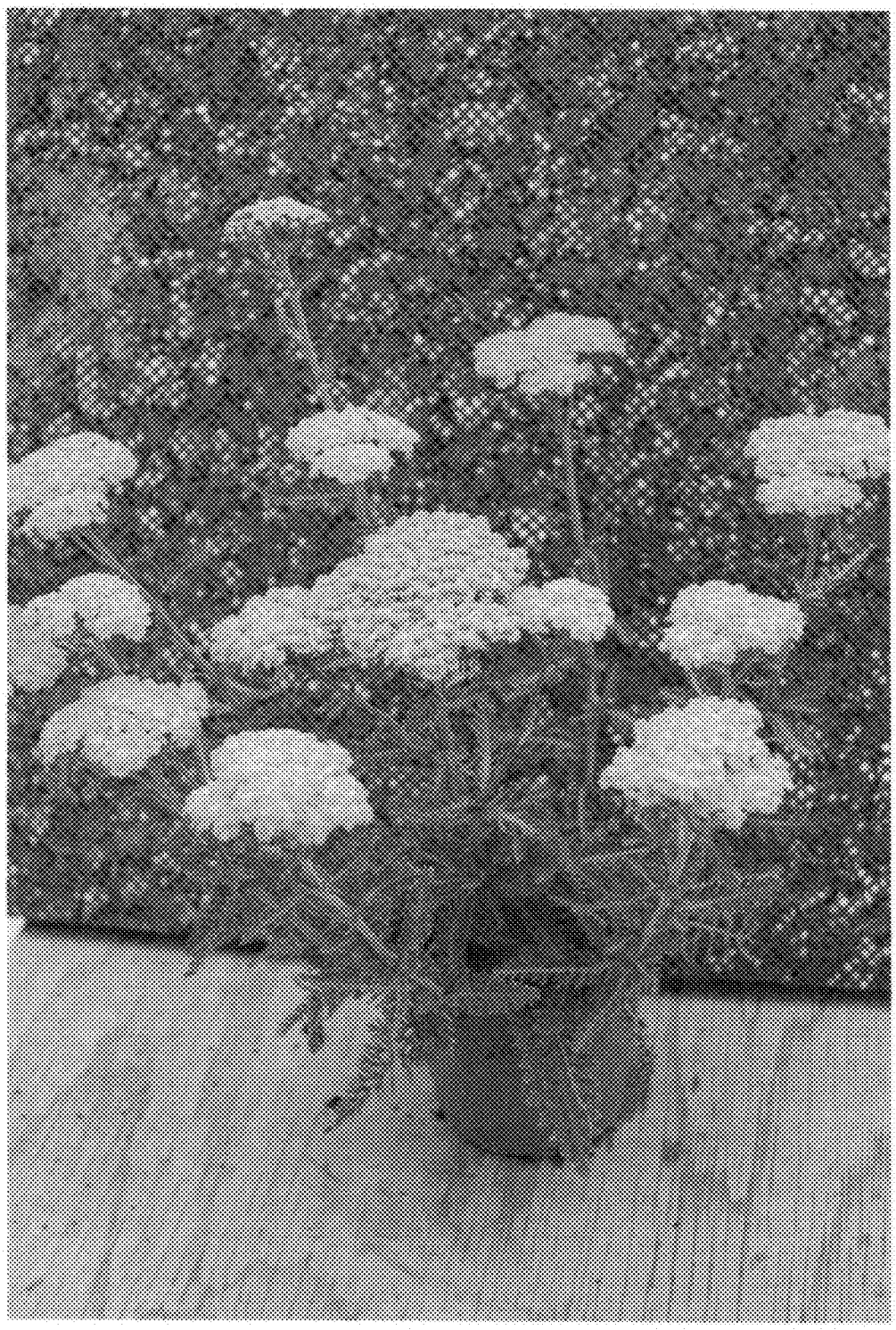

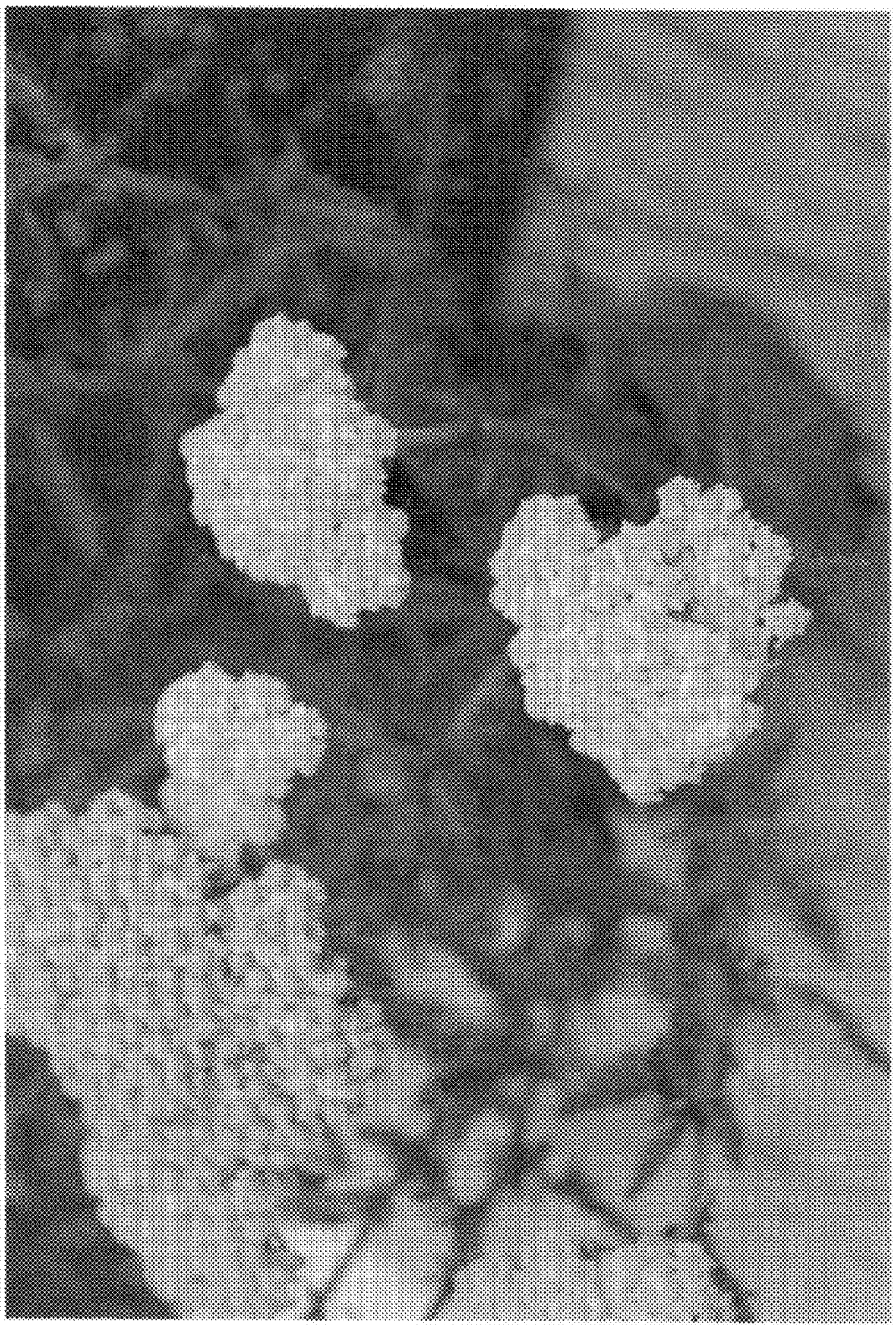

* * * * *